United States Patent [19]
Trauffer et al.

[11] Patent Number: 5,885,538
[45] Date of Patent: *Mar. 23, 1999

[54] METHOD AND COMPOSITION FOR THE REGENERATION OF AN AMINAL COMPOUND

[75] Inventors: Edward A. Trauffer, Rydal; Muge Caglar, Ardmore, both of Pa.

[73] Assignee: Quaker Chemical Corporation, Conshohocken, Pa.

[ * ] Notice: The term of this patent shall not extend beyond the expiration date of Pat. No. 5,698,171.

[21] Appl. No.: 886,868

[22] Filed: Jul. 2, 1997

[51] Int. Cl.⁶ ................................. B01D 53/52
[52] U.S. Cl. ................. 423/220; 423/224; 423/226; 423/573.1; 423/576.4; 423/576.7; 564/396; 564/397; 564/471; 564/472
[58] Field of Search .................. 423/220, 224, 423/226, 242.1, 573.1, 576.4, 576.7; 564/396, 397, 471, 472

[56] References Cited

U.S. PATENT DOCUMENTS

| | | |
|---|---|---|
| 2,776,870 | 1/1957 | Fischer . |
| 3,622,273 | 11/1971 | Roberts et al. . |
| 4,002,727 | 1/1977 | Sonoda et al. . |
| 4,076,621 | 2/1978 | Hardison . |
| 4,112,051 | 9/1978 | Sartori et al. . |
| 4,414,194 | 11/1983 | Blytas . |
| 4,436,714 | 3/1984 | Olson . |
| 4,455,287 | 6/1984 | Primack et al. . |
| 4,541,998 | 9/1985 | Weber . |
| 4,624,838 | 11/1986 | Pan et al. . |
| 4,647,397 | 3/1987 | Starkston et al. . |
| 4,775,519 | 10/1988 | Yit Nieh . |
| 4,978,512 | 12/1990 | Dillon . |
| 5,128,049 | 7/1992 | Gatlin . |
| 5,160,714 | 11/1992 | Hardison . |
| 5,273,734 | 12/1993 | Sawyer et al. . |
| 5,347,003 | 9/1994 | Trauffer et al. . |
| 5,405,591 | 4/1995 | Galloway . |
| 5,478,536 | 12/1995 | Galloway . |
| 5,698,171 | 12/1997 | Trauffer et al. ............ 423/220 |

FOREIGN PATENT DOCUMENTS

| | | |
|---|---|---|
| 4-290547 | 10/1992 | Japan . |
| 2103645 | 2/1983 | United Kingdom . |

OTHER PUBLICATIONS

"Gas Purification" by Kohl et al.; 4th Ed., Gulf Publishing Co., Houston, Texas, USA (1985, no month given), pp. 486–488).

DeBerry, *Chemical Issues and Evolution of Liquid Redox Sulfur Recovery Processes*, presented at 1995 Gas Research Institute Sulfur Recovery Conference, (Sep. 24–27, 1995).

Cotton et al., Advanced Inorganic Chemistry, 4th Edition, John Wiley & Sons, pp. 118–119 (1980).

Oosterwouder et al., Dow Chemical, S.P., *Sulferox Process Technology and Application Update Sulfur Recovery Conference*, presented at Gas Research Institute's 7th Sulfur Recovery Conference, pp. 2–10 (Sep. 1995).

Nagl, *ARI Lo–Cat/ARI Lo–Cat II Application and Process Technology Update*, presented at Gas Research Institute's 7th Sulfur Recovery Conference, p. 3 (Sep. 1995).

Demmink et al, University of Groningen, Netherlands, *Gas Desulfurisation with Iron Chealates: A Comprehensive Model for Ferrous NTA Regeneration*, presented at Gas Research Institute;s 7th Sulfur Recovery Conference, section 5.3 (Sep. 1995).

*Primary Examiner*—Shailendra Kumar
*Attorney, Agent, or Firm*—Ratner & Prestia

[57] ABSTRACT

The present invention provides a method and composition regeneration of an aminal that has previously been reacted with a sulfide selected from hydrogen sulfide and mercaptans. The method includes contacting a scavenging mixture which includes an aminal, and an oxidation catalyst with a gas such as air, oxygen enriched air, oxygen, ozone enriched air and ozone. The composition includes an aminal, and an oxidation catalyst. The method and composition are useful for the regeneration of an aminal base sulfur scavenging compound.

33 Claims, No Drawings

METHOD AND COMPOSITION FOR THE REGENERATION OF AN AMINAL COMPOUND

FIELD OF THE INVENTION

The present inventions relates to a method and composition for the regeneration of an aminal that had previously been at least partially reacted with a sulfide. The method is particularly useful because it allows for economic in situ regeneration of the at least partially reacted aminal.

BACKGROUND OF THE INVENTION

Hydrogen sulfide is a toxic, corrosive and malodorous compound. It may be found in a variety of liquid and gaseous media such as natural gas, petroleum, refinery gas streams, carbon dioxide, hydrogen, coal gas streams, gas streams from viscose rayon production, tars and asphalt, shale gas, coke oven gases, ammonia synthesis gas, rubber vulcanization streams, gases from sulfurization plants, turpentine production, pulp and paper mill effluent, sewage, brine drilling mud, land fills, phosphoric acid production gas streams, and other industrial gas streams and effluents. It is also found in the tail gases and liquids of some hydrogen sulfide scrubbing processes such as Claus plants and amine scrubbing units.

Hydrogen sulfide is an undesirable contaminant and its release into the environment is strictly controlled by the Environmental Protection Agency, the Department of Environmental Resources, as well as by other regulatory agencies throughout the world. Hydrogen sulfide not only has an offensive odor, but it has also been linked to the formation of acid rain.

Methods for removing hydrogen sulfide may be generally classified as regenerative and non-regenerative. Regenerative processes are generally more desirable because waste products are recycled. By regenerating sulfur scavenging compounds and thereby recycling the waste products, the cost, both economically and environmentally, of replenishing spent chemicals in the process and disposing of the waste products is lessened or eliminated. It is even more desirable to recover the sulfur scavenged during the hydrogen sulfide scavenging reaction in a useful form.

Various amines and alkanolamines, which may be regenerated, have been used to remove acids, such as hydrogen sulfide from gas streams. U.S. Pat. No. 2,776,870 discloses that aqueous amines and alkanolamines are useful for removing acids from a gaseous mixture. Hydrogen sulfide may be selectively removed from gas streams containing carbon dioxide by use of triethanolamine or methyldiethanolamine.

British Published Patent Specification No. 2103645 discloses that hydrogen sulfide and carbon dioxide may be removed from a gas mixture by contacting the mixture with a solvent comprising a tertiary amine and a physical absorbent. Suitable physical adsorbents include N-methylpyrrolidone and sulfolane.

U.S. Pat. No. 4,112,051 discloses a process for removing acidic gases from a gaseous mixture with an amine-solvent liquid absorbent comprising (1) an amine comprised of at least about 50 mole percent of a steric hindered amine; and (2) a solvent for the amine mixture which is also a physical absorbent for the acid gases. Suitable steric hindered amines include various piperidine compounds. Suitable solvents include sulfones and pyrrolidone and piperidone compounds, to name a few.

U.S. Pat. No. 4,978,512 discloses methods for reducing the levels of hydrogen sulfide and organic sulfides in a hydrocarbon stream by contacting the stream with a composition comprising the reaction products of a lower alkanolamine with a lower aldehyde. Suitable reaction products include mixtures of triazine and bisoxazolidine compounds.

U.S. Pat. No. 4,647,397 discloses a process and composition for removing hydrogen sulfide and similar sulfides from a gas stream. The gas stream is contacted with a substituted aromatic nitrile having an electron-attracting substitutent on the aromatic ring at least as strong as a halogen and an organic tertiary amine in an inert organic solvent, such as N-methyl-2-pyrrolidone. The spent contacting solution may be regenerated by heating the solution above the decomposition temperature of the reaction products to separate the sulfides from the liquid phase absorbent solution.

U.S. Pat. No. 4,775,519 discloses a continuous process for removing acid gas components from a gas stream by counter-currently contacting the stream with an aqueous solution of a mixture of N-methyldiethanolamine (MDEA) with imidazole or a methyl substituted imidazole. The gas is de-absorbed from the MDEA and the imidazole by reducing the pressure and causing the gas to flash.

U.S. Pat. No. 4,624,838 discloses a process for removing acid gases from a gaseous stream by contacting the stream with an aqueous scrubbing solution containing a hetero amine comprising either a five- or six-membered ring having a pKa no greater than about 8. Preferred hetero amines include imidazole and piperazine compounds.

U.S. Pat. No. 5,128,049 discloses a method for reducing the hydrogen sulfide content of hydrocarbon-containing fluids and aqueous solutions by injections of a dilute solution of a scavenging agent. Suitable scavenging agents include hexahydro-1,3,5-tris(2-hydroxyethyl)-s-triazine and various other compounds.

U.S. Pat. No. 5,347,003 describes a regenerative method where an N—C—N compound is regenerated from a product of a sulfur scavenging reaction, in which said N—C—N compound removes a sulfur atom from a sulfur compound to form the original N—C—N compound.

U.S. Pat. No. 3,622,273 discloses a regenerative method for the removal of hydrogen sulfide from a gaseous stream wherein the gaseous stream is contacted with a solution containing, by weight, from 0.005 to 20 percent of a ferric ion complex, from 25.0 to 99.945 percent of water and from 0.05 to 10.0 percent of a buffering agent selected from the group consisting of alkali metal carbonate.

There are numerous patents dealing with the removal of hydrogen sulfide from liquid or gas streams with various metal chelates through redox reactions with a higher oxidation state of the metal followed by oxidative regeneration through the use of air. As a sampling: U.S. Pat. No. 4,076,621 deals with iron chelates for the removal of hydrogen sulfide from water; U.S. Pat. No. 4,414,194 deals with iron chelates with alcohol as a crystal modifier; U.S. Pat. No. 4,436,714 deals with the use of metal chelates followed by electrolytic regeneration. All of the patents related to the use of metal chelates have in common the use of the metal ion to directly oxidize hydrogen sulfide to a higher oxidation state. A draw back of this technology is the long contact time required in order to achieve efficient removal of hydrogen sulfide from the gas streams and the cost of the reactants. Another drawback is the tendancy of the metal chelates to precipitate out of solution with pH changes or over time due to the relative instability of the chelated metal ions.

U.S. Pat. No. 4,455,287 describes a method of oxidizing hydrogen sulfide in gases to elemental sulfur by a continuous polyvalent metal catalytic liquid phase oxidation with catalysts such as iron chelate solutions in which the solution is stabilized by incorporating a general purpose biocide at a level below the kill concentration of the biocide. Typical biocide concentrations were in the range of low parts per million by weight of solution. This is different from the present invention in that the aminal compounds are not general purpose biocides, although at least one has been used as a fungicide. None of the biocides described are known to reduce the levels of hydrogen sulfide. Additionally, the levels of biocide used were far too low to achieve a measurable reduction of hydrogen sulfide, even if they were reactive.

There is a long-felt need in the art for improved, economic methods for regenerating sulfur scavenging compounds. Regenerating such compounds is not only environmentally desirable, but is also cost efficient and may reduce or eliminate the need for expensive processing equipment. In addition, since the scavenging compounds are regenerated, the need for purchasing replacement scavenging compound is greatly reduced.

An even greater benefit may be realized when the scavenged compounds are converted to a commercially useful form. The regeneration of sulfur compounds in such form provides a further financial incentive for the scavenging of such compounds and even further reduces the burden on waste disposal systems.

DEFINITIONS

As used herein the term "sulfides" is defined to mean compounds selected from the group including hydrogen sulfide and mercaptans.

As used herein the term "spent" is defined to mean at least partially reacted with a sulfide for the formation of at least some hetero compound.

As used herein the term "vessel" is defined to mean any scrubber, tank or pipe in which gas may be contained or through which it may be passed.

SUMMARY OF THE INVENTION

The present invention provides a method and composition for the regeneration of an aminal. The method includes contacting a scavenging mixture which includes an aminal, and an oxidation catalyst with a gas such as air, oxygen enriched air, oxygen, ozone enriched air and ozone. The composition includes an aminal, and an oxidation catalyst.

An aminal is a reaction product between an aldehyde and a nitrogen containing compound selected from the group consisting of primary amines, secondary amines and ammonia. Typical aldehydes include formaldehyde, paraformaldehyde, glyoxal, acetaldehyde, butyraldehyde, benzaldehyde, N-(2-hydroxyethyl)dioxazine and oleyl aldehyde. Typical nitrogen containing compounds include ammonia, methylamine, ethylamine, propylamine, isopropyl amine, oleylamine, ethylene diamine, diethylene triamine, dimethylamine, diethylamine, monoethanolamine, diethanolamine, morpholine, piperazine, 3-ethoxypropylamine, 1-methoxyisopropylamine, 2-methoxyethylamine, thiomonoethanolamine and chlorooleylamine. The oxidation catalyst is an oxidizing agent with at least mild oxidation properties. Typical oxidation catalysts are selected from the group consisting of halides, quinones, organic peroxides, organic peroxyacids, inorganic peroxides, organic oxides, hydrazines, amino acids, amides, carbamates, carbazides, perchlorates, polyvalent metals and compounds thereof, inorganic oxidizers and organic dyes. It is preferred that the catalysts be water soluble in order to better facilitate the regeneration step.

DESCRIPTION OF THE PREFERRED EMBODIMENTS

The present method describes a means for the removal of hydrogen sulfide from a gaseous stream with subsequent regeneration of the reaction mixture. E. A. Trauffer and R. D. Evans in U.S. Pat. No. 5,347,003, incorporated herein by reference, describe a method for regenerating a sulfur scavenging compound from a product of a sulfur scavenging reaction wherein the sulfur scavenging compound is represented by an aminal of the formula (I):

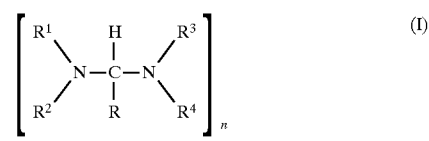

Each of $R^1$, $R^2$, $R^3$, $R^4$, and R is independently selected from the group consisting of (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of $R^1$, $R^2$, $R^3$, $R^4$, and R.

Examples of aminals which are useful as the initial scavenging step include various triazines, such as 1,3,5-tris (2-hydroxyethyl)hexahydro-s-triazine, and trimethyl triazine, bisoxazolidines, such as N,N'-methylene bisoxazolidine, bis(dibutylamino)methane and bis(di-2-hydroxyethylamino)methane, bis(morpholino)methane, and 1,3,6,8-tricyclotetraaza[4,4,1,1$^{3,8}$]-dodecane.

At least part of the aminal is first reacted with hydrogen sulfide from the hydrogen sulfide containing stream forming a hetero compound. The hetero compound is then reacted with an alkaline compound to regenerate the spent aminal.

While efficient, the regenerative method described requires the addition of an alkaline material in a quantity that is proportional to the amount of hydrogen sulfide that has been reacted.

Our co-pending application Ser. No. 08/587,837, incorporated herein by reference, discloses a superior method and composition for the removal of sulfides from gaseous streams. The method includes contacting the sulfide-containing gas stream with an aqueous scavenging mixture which includes an aminal, an inorganic ion and an oxidation catalyst; regenerating at least a portion of the aminal with a gas such as air, oxygen enriched air, oxygen, ozone enriched air and ozone; and returning at least a portion of the aqueous scavenging mixture to the contacting zone.

While effective, the method and composition still requires the addition of an inorganic ion to the scavenging mixture, similar to that used in U.S. Pat. No. 5,347,003. The use of an inorganic ion adds a level of complexity to the manufacture.

We have discovered that sulfur can be directly oxidized from a hetero compound without the addition of an inorganic base. This is particularly surprising since analogous thioethers do not react with oxidizing agents to form elemental sulfur, but rather normally react to form sulfones and sulfoxides in which the sulfur atom remains in the organic molecule and is oxidized to a higher oxidation state. In the present method, sulfur is eliminated in the form of elemental sulfur and is subsequently replaced by a nitrogen containing compound. It is possible that this unusual reaction occurs due to a stabilized transition state as discussed below. It is therefor likely that the presence of nitrogen in the beta position with respect to sulfur in the hetero compound plays a significant role in the regeneration reaction.

The present method allows for the direct oxidation of the hetero compound resulting in the formation of elemental sulfur and the regenerated aminal. This is achieved by preparing a composition containing the aminal, the oxidation catalyst, and optionally, diluent water. Improved economy is achieved by providing a method in which a sub-stoichiometric quantity of oxidation catalyst may be used. The composition may also contain a variety of other components that may impart additional desirable properties, including but not limited to, defoamers, crystal modifiers, antifreeze compounds and scents.

In the present method, the aminal is a reaction product between (a) a hydrous or anhydrous aldehyde of formula (II):

(II)

Where R is selected from the group consisting of (i) hydrogen; (ii) a substituted or unsubstituted, saturated or unsaturated, linear, branched or cyclic hydrocarbon chain of 1 to 50 carbons; (iii) a substituted or unsubstituted, saturated or unsaturated, linear, branched or cyclic hydrocarbon chain of 1 to 50 carbons comprising at least one heteroatom selected from the group consisting of nitrogen, oxygen, sulfur and halogen; (iv) a substituted or unsubstituted polymeric chain; (v) a substituted or unsubstituted dimer (vi) a mono or polyaldehyde; and (b) a nitrogen containing compound of formula (III)

(III)

Wherein $R^1$ and $R^2$ are independently selected from the group consisting of (i) hydrogen; (ii) a substituted or unsubstituted, saturated or unsaturated, linear, branched or cyclic hydrocarbon chain of 1 to 50 carbons; (iii) a substituted or unsubstituted, saturated or unsaturated, linear, branched or cyclic hydrocarbon chain of 1 to 50 carbons comprising at least one heteroatom selected from the group consisting of nitrogen, oxygen, sulfur and halogen; (iv) a substituted or unsubstituted polymeric chain; and (v) a direct bond to any other of $R^1$ and $R^2$.

Examples of aldehydes suitable for the present invention include formaldehyde, paraformaldehyde, glyoxal, acetaldehyde, butyraldehyde, benzaldehyde, N-(2-hydroxyethyl)dioxazine and oleyl aldehyde. Examples of nitrogen containing compounds suitable for the present invention include, but are not limited to: ammonia, methylamine, ethylamine, propylamine, isopropyl amine, oleylamine, ethylene diamine, diethylene triamine, dimethylamine, diethylamine, monoethanolamine, diethanolamine, morpholine, piperazine, 3-ethoxypropylamine, 1-methoxyisopropylamine, 2-methoxyethylamine, thiomonoethanolamine and chlorooleylamine.

The nitrogen containing compound and the aldehyde of the present invention may be reacted in any molar ratio with a preferred ratio being from 1 mole aldehyde to 10 moles nitrogen containing compound to 10 moles aldehyde to 1 mole nitrogen containing compound, a more preferred ratio being from 1 mole aldehyde to 5 moles nitrogen containing compound to 5 moles aldehyde to 1 mole nitrogen containing compound, an even more preferred ratio being 1 mole aldehyde to 3 moles nitrogen containing compound to 3 moles aldehyde to 1 mole nitrogen containing compound and a most preferred ratio being 1 mole aldehyde to 1 mole nitrogen containing compound.

The aminal formed from the reaction of the aldehyde and nitrogen containing compound are dependent upon the selected nitrogen containing compound, the selected aldehyde and the ratios of each selected, as is self evident to those of ordinary skill in the art. Similarly, mixtures of the above aldehydes and nitrogen containing compounds may also be reacted in order to form singular, or mixtures of, various aminals as is also evident to one of ordinary skill in the art.

The reaction of the nitrogen containing compound and the aldehyde listed above will typically result in the formation of an aminal. Aminals typical of those formed in the described reaction are of the type as in formula I, IV, formula V, or mixtures thereof as is evident to one of ordinary skill in the art where formula I, IV and formula V are represented by:

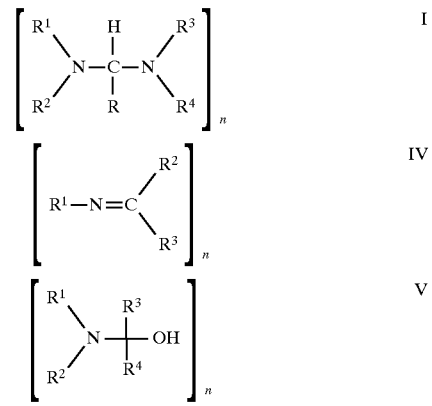

Where n is an integer from 1 to 1000 and each of $R^1$, $R^2$, $R^3$, $R^4$, and R is independently selected from the group consisting of (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of $R^1$, $R^2$, $R^3$, $R^4$, and R.

Non-limiting examples of aminals which are useful for the present invention include various triazines, such as 1,3,5-tris(2-hydroxyethyl)hexahydro-s-triazine, and trimethyl triazine, bisoxazolidines, such as N,N'-methylene bisoxazolidine, bis(morpholino)methane, 1,3,6,8-tricyclotetraaza[4,4,1,1$^{3,8}$]-dodecane, non-generic aminals such as 2,7-dioxa-5,10diazabicyclo[4.4.0]dodecane, methylaminomethanol, ethylmethyleneimine, isopropylmethyleneimine, and hexamethylenetetramine.

Suitable oxidation catalysts include, but are not limited to: halides, quinones, organic peroxides, organic peroxyacids, inorganic peroxides, organic oxides, hydrazines, amino acids, amides, carbamates, carbazides, perchlorates, polyvalent metals and compounds thereof, inorganic oxidizers and organic dyes. Specific examples of oxidation catalysts include 1,2,Naphthaquinone-4-sulfonic acid sodium salt, 4-amino-3-hydrazino-5-mercapto-1,2,4-triazole, 2-hydroxy-1,4-naphthaquinone, and metachloroperbenzoic acid.

The oxidation step of the present invention can be accomplished through the use of very mild oxidation catalysts. It is believed that the ease of oxidation of the sulfur from the spent aminal is due to stabilization of the transition state due to imine formation. A specific, non-limiting representation can be seen in scheme (I).

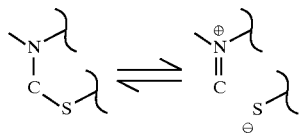

As a result, virtually any chemical compound with even mild oxidative ability is suitable to act as an oxidation catalyst in the present invention.

An example of a typical spent aminal, 5,6-dihydro-5-(2-hydroxyethyl)-4H-1,3,5-dithiazine shows an irreversible oxidation wave with a peak potential of about 0.6 volts vs. NHE (standard hydrogen electrode) as determined by cyclic voltammetry at a scan rate of 10 millivolts/second. A second irreversible oxidation wave appears at about 1.5 volts. Oxidation reactions of the solvent are significant at this potential, and the second wave is fully resolved only after a passivating film covers the electrode. This second wave likely corresponds to the oxidation of the 1,3,5-(2-hydroxyethyl)-hexahydro-s-triazine that is formed from the oxidation of the dithiazine. Chronopotentiometry experiments demonstrated a slight oxidizing current could be achieved at a potential of 0.18 volts. The reaction rate is slow at such low potentials, but it increases significantly at a potential of about 0.3 volts. Zero current was maintained at a potential of about 0.02 volts. This indicates that any compound with a standard reduction potential greater 0.02 volts is suitable for the conversion of spent aminal to aminal.

Oxygen is well suited to drive the oxidation of the spent aminal since the half reaction $O_2 + 4e^- \rightarrow 4 OH^-$ has a standard reduction potential of 0.4 volts. However, the reaction between oxygen by itself and the spent aminal is not fast enough to drive the reaction at an acceptable rate. The use of a catalytic amount of an oxidizing agent in the present invention produces a suitable reaction rate.

Virtually any oxidizing agent that can be regenerated by oxygen will catalyze the reaction to accelerate regeneration of the aminal. There is no need for the oxidizing agent to have a standard reduction potential greater than 0.18 volts. As an example, anthraquinone-2,6-disulfonate, which has a formal potential of −0.325 volts in alkaline solutions, is quite effective in catalyzing the conversion of 5,6-dihydro-5-(2-hydroxyethyl)-4H-1,3,5-dithiazine to the 1,3,5-(2-hydroxyethyl)-hexahydro-s-triazine. It is preferred that the selected oxidation catalyst has a standard reduction potential of at least −0.4 volts. It is more preferred that the selected oxidation catalyst has a standard reduction potential from 0.0 to 0.9 volts. It is most preferred that the selected oxidation catalyst has a standard reduction potential between 0.3 and 0.8 volts.

The overall reaction method involves contacting the composition which contains the aminal and the oxidation catalyst with a gas containing a sulfide selected from hydrogen sulfide and mercaptans, in order to react at least some of the aminal with the sulfide, and forming at least some spent aminal in the form of a sulfur containing compound. The sulfur containing compound is then reacted with the oxidation catalyst and an oxidation source selected from gases containing air, oxygen, ozone, or mixtures thereof, to oxidize the sulfur from the sulfur containing compound in the form of elemental sulfur or some higher oxidation state of sulfur. The oxidation is carried out through the aid of the oxidation catalyst in solution to better facilitate oxidation.

The reaction is believed to proceed as in the following specific, non limiting example:

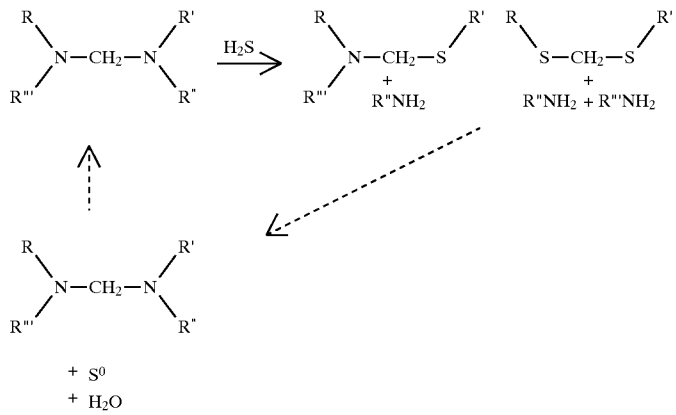

It is important to note that each of the components of the mixture may be added in either their initially reactive, or reacted form since all of the reactants in solution are regenerated in at least one step of the process. The oxidation catalyst maybe added in either an oxidized or reduced form. Similarly, the aminal may be added in spent or fresh form.

Upon regeneration, the identical aminal that was used in the starting composition is not necessarily formed. The regenerated compound may be of a different chemical structure due to rearrangement, disproportionation or other chemical transformations. However, whatever the structure, the regenerated compound will react in the desired manner to scavenge hydrogen sulfide and mercaptans.

The present method provides for a superior regenerative sulfide scavenging system due to the rapid reaction of the aminal with hydrogen sulfide. The rapid reaction time allows for the design of relatively small contact equipment for low capital cost. Additionally the process may be carried out in virtually any existing equipment that has been designed for the removal of hydrogen sulfide from gasses by metal chelates. Such processes include, but are not limited to: Stretford, Lo-Cat and Sulferox equipment. Existing non-regenerative scrubber equipment may also be utilized by adding a regeneration loop in which the at least partially spent aminal is drained from the scrubber, directed to the regeneration equipment, and then returned to either a storage tank or directly to the contact scrubber. Regeneration and scavenging can also be accomplished in one vessel where the oxygen content of the gas stream passing through the liquid is at least as high as the concentration of hydrogen sulfide in the gas stream.

The method and composition of the present invention offer several distinct advantages over common metal-chelate systems. Metal-chelates remove hydrogen sulfide through a redox reaction between the oxidized form of the metal and the hydrogen sulfide in a contacting vessel. Elemental sulfur is formed in the contacting vessel as a result of this reaction. Sulfur fouling is a common problem that plagues these systems. By contrast, elemental sulfur is not formed upon contact with the scavenging composition of the present invention when the oxidation catalyst is in a reduced state. This allows for a much more controlled precipitation of the sulfur, upon contact with oxygen. The sulfur can therefore be formed in a separate vessel, or even at a distant time, if so desired.

Metal-chelates also rely heavily on the chelant to keep the metal in solution. The system is pH dependent and subject to degradation due to free radical reactions, both of which may render it less efficient or inoperable. This problem is avoided in the present invention by allowing for the selection of a water soluble oxidation catalyst that will not separate out from the system. The present invention also does not rely on heavy dilution of the scavenging system. This allows for the use of significantly smaller equipment with increased efficiency.

In a typical application fresh, or fully or partially regenerated aminal is contacted with a hydrogen sulfide or mercaptan containing gas stream for a time sufficient to lower the levels of hydrogen sulfide or mercaptans to the desired amount. Some or all of the resultant at least partially spent aminal is removed from the scrubber and transferred to an oxidation zone. The solution is contacted with an oxidizing gas such as air, oxygen, ozone, or mixtures thereof, in the presence of an oxidation catalyst for a period of time to allow for the partial or complete regeneration of the aminal. In the oxidation tank, the sulfur in the spent aminal is oxidized to elemental sulfur and other higher oxidation states of sulfur. The resultant slurry containing elemental sulfur and at least partially regenerated aminal is optionally passed through a solids separation stage where at least a portion of the solid elemental sulfur is removed. Solid separation may be achieved by any means known in the art including, but not limited to, settling, gravity filtration, vacuum filtration, centrifugation, filter pressing, or combinations thereof. The solution is then passed to a storage tank or returned to the scrubber. The process may be carried out either continuously or in a batch operation. A certain amount of volume of the liquid is lost in the solid separation stage. Make-up product may be added at any point in the process to replace the lost volume. A preferred injection point of make-up material is prior to the scrubber. This will allow for the highest concentration of aminal in the gas contacting stage. Equipment or other considerations may require addition of make-up at other points.

As with virtually all catalytic processes, there will be some depletion or deactivation of the oxidation catalyst in the process of the present invention. The replacement of the depleted catalyst is most conveniently added as part of the make-up system described. It may optionally be added at a different point in the process as a matter of convenience.

The solution may also be applied in an auto circulation type equipment in which scrubbing and oxidation are carried out in the same vessel as described in U.S. Pat. No. 5,160,714, incorporated herein by reference. Similar effects may be achieved where the sulfide containing gas stream contains a sufficient amount of oxygen to allow for scrubbing and oxidation in the same vessel. The oxygen may be already present, or may be combined with the sulfide containing gas stream through the introduction of air, or an alternate source of oxygen gas.

It is recognized that in a continuous process, there will always be at least some spent aminal present at all points in the system if the equipment is optimized for capital cost and material cost. The presence of spent aminal will have no deleterious effect on the reactions in the system. Under these conditions the solution will also contain the reduced form of the oxidation catalyst. The presence of the reduced form of the oxidation catalyst will not result in a reduction in the amount of hydrogen sulfide in the scrubber section of the apparatus since it is unreactive with hydrogen sulfide in this state.

The ratios of aminal to oxidation catalyst may vary dependent on the physical parameters of the installed equipment. In general the quantity of oxidation catalyst should be minimized due to its relatively higher cost. Ratios to be utilized are best determined on a molar basis. The effective equivalent weight of the aminal can most easily be determined by reacting it to completion with a measured quantity of hydrogen sulfide and then dividing the weight of the aminal utilized by the moles of hydrogen sulfide consumed. Ideally the hydrogen sulfide source should be the gas stream to be treated. The equivalent weights of the oxidation catalysts are well known in the art.

It is preferred that from 1 to 10000 molar equivalents of aminal is utilized with from 1 to 10000 equivalents of oxidation catalyst. In a more preferred method, from 1 to 10000 molar equivalents of aminal is utilized with from 1 to 100 molar equivalents of oxidation catalyst. In a most preferred method from 1 to 10000 molar equivalents of aminal is utilized with from 1 to 10 molar equivalents of oxidation catalyst.

Water is optionally present in the composition of the present method as a diluent. The presence of water will also serve to aid in the separation of elemental sulfur by lowering the viscosity of the solution. Water may be present in any quantity, with a preferred quantity being up to 99.5% by weight, a more preferred quantity being from 25% by weight to 99.5% by weight and a most preferred being from 50% by weight to 95% by weight.

The present method will now be illustrated in more detail by reference to the following, specific, non-limiting examples.

EXAMPLE 1

Five grams of a 43% solution of 1,3,5-tri(2-hydroxyethyl) hexahydro-s-triazine, available commercially from Quaker Chemical Corp. that had been previously reacted with 99.5% hydrogen sulfide, commercially from Aldrich Chemical of Milwaukee Wis., to completion, was mixed with 0.2 grams of 4-amino-3-hydrazino-5-mercapto-1,2,4-triazole (99%), available commercially from Aldrich Chemical of Milwaukee Wis. Ten grams of distilled water was added to this mixture. The solution was then stirred and aerated in a 500 ml bottle by bubbling air into the mixture at room temperature (approx. 20° C.) at a flow rate of 33 ml/sec for two days. After two days the 1,3,5-tri(2-hydroxyethyl)hexahydro-s-triazine solution was completely regenerated. The solution was then reacted with 0.7 grams of 99.5% hydrogen sulfide gas, available commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The aeration cycle was repeated and the solid precipitate (0.4 grams) was vacuum filtered with a 25 micron glass filter.

EXAMPLE 2

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.2 grams of Maleic acid (99%), available commercially from Aldrich Chemical of Milwaukee Wis. Ten grams of distilled water was added to this mixture. The solution was then stirred and aerated in a 500 ml bottle by bubbling air into the mixture for 2 days at room temperature (approx. 20° C.) at a flow rate of 33 ml/sec. At the end of the aeration process the 1,3,5-tri(2-hydroxyethyl)hexahydro-s-triazine solution was 58% regenerated.

EXAMPLE 3

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 1.1 grams of Potassium Permanganate (15.804%), available commercially from Fisher Scientific Company of Fair Lawn, N.J. Ten grams of distilled water was added to this mixture. The solution was then stirred and aerated in a 500 ml bottle by bubbling air through the mixture at room temperature (approx. 20° C.) at a flow rate of 33 ml/sec. After two days the 1,3,5-tri(2-hydroxyethyl)hexahydro-s-triazine solution was completely regenerated. The solution was then reacted with 0.9 grams of 99.5% hydrogen sulfide gas, available commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The aeration cycle was repeated and the 1,3,5-tri(2-hydroxyethyl)hexahydro-s-triazine solution was 28% regenerated.

EXAMPLE 4

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.2 grams of 5-amino valeric acid (97%), available commercially from ACROS Organics of Pittsburgh Pa. Fifteen grams of distilled water was added to this mixture. The solution was then stirred and aerated in a 500 ml bottle by bubbling air into the mixture for 12 hours at room temperature (approx. 20° C.) at a flow rate of 33 ml/sec. At the end of the aeration process the 1,3,5-tri(2-hydroxyethyl)hexahydro-s-triazine solution was 68% regenerated.

EXAMPLE 5

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.15 grams of hydrazine dihydrochloride (99.9%), available commercially from Aldrich Chemical of Milwaukee Wis. Ten grams of distilled water was added to this mixture. The solution was then stirred and aerated in a 500 ml bottle by bubbling air into the mixture for 12 hours at room temperature (approx. 20° C.) at a flow rate of 33 ml/sec. At the end of the aeration process the 1,3,5-tri(2-hydroxyethyl)hexahydro-s-triazine solution was 59% regenerated.

EXAMPLE 6

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.26 grams of 2,4,6-trihydroxybenzoic acid monohydrate (90%), available commercially from Aldrich Chemical of Milwaukee Wis. Ten grams of distilled water was added to this mixture. The solution was then stirred and aerated in a 500 ml bottle by bubbling air into the mixture for 12 hours at room temperature (approx. 20° C.) at a flow rate of 33 ml/sec. At the end of the aeration process the 1,3,5-tri(2-hydroxyethyl)hexahydro-s-triazine solution was 10% regenerated.

EXAMPLE 7

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.20 grams of 2-hydroxy-1,4-naphthoquinone (97%), available commercially from Aldrich Chemical of Milwaukee Wis. Fifteen grams of distilled water was added to this mixture. The solution was then stirred and aerated in a 500 ml bottle by bubbling air into the mixture for 2.5 hours at room temperature (approx. 20° C.) at a flow rate of 33 ml/sec. At the end of the aeration process the 1,3,5-tri(2-hydroxyethyl)hexahydro-s-triazine solution was 43% regenerated.

EXAMPLE 8

Five grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.5 grams of anthraquinone-2,6-disulfonic acid disodium salt, available commercially from Aldrich Chemical of Milwaukee Wis. Fifteen grams of distilled water was added to this mixture. The solution was then stirred and aerated in a 500 ml bottle by bubbling air into the mixture for 4 hours at room temperature (approx. 20° C.) at a flow rate of 33 ml/sec. At the end of the aeration process the 1,3,5-tri(2-hydroxyethyl)hexahydro-s-triazine solution was 74% regenerated.

EXAMPLE 9

Seven and a half grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.17 grams of 1,4-benzoquinone (98%), available commercially from Aldrich Chemical of Milwaukee Wis. Twenty-three grams of distilled water was added to this mixture. The solution was then stirred and aerated in a 500 ml bottle by bubbling air into the mixture for 2 days at room temperature (approx. 20° C.) at a flow rate of 33 ml/sec. At the end of the aeration process the 1,3,5-tri(2-hydroxyethyl) hexahydro-s-triazine solution was 91% regenerated. The solution was then reacted with 0.7 grams of 99.5% hydrogen sulfide gas, available commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The aeration cycle was repeated and the 1,3,5-tri(2-hydroxyethyl)hexahydro-s-triazine solution was completely regenerated. The solution was then reacted with 0.6 grams of 99.5% hydrogen sulfide gas by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector.

EXAMPLE 10

Twenty-five grams of a 43% solution of 1,3,5-tri(2-hydroxyethyl)hexahydro-s-triazine, available commercially from Quaker Chemical Corp. was mixed with 1.3 grams of 1,4-benzoquinone (98%), available commercially from Aldrich Chemical of Milwaukee Wis. Twenty three grams of distilled water was added to this mixture. The solution was then reacted with 7.4 grams of 99.5% hydrogen sulfide gas, available commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The solution was then stirred and aerated in a 500 ml bottle by bubbling air into the mixture for 7 hours at room temperature (approx. 20° C.) at a flow rate of 33 ml/sec. At the end of the aeration process the 1,3,5-tri(2-hydroxyethyl)hexahydro-s-triazine solution was 80% regenerated. The solution was then reacted with 2.3 grams of 99.5% hydrogen sulfide gas, available commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. Two grams of sodium bicarbonate, available commercially from ARM & HAMMER of Princeton N.J., and two grams of 50% sodium hydroxide solution, available commercially from Aldrich Chemical of Milwaukee Wis., were added to the solution and the aeration cycle was repeated for 21 hours. The 1,3,5-tri(2-hydroxyethyl) hexahydro-s-triazine solution was 93% regenerated. The solution was then reacted with 1.3 grams of 99.5% hydrogen sulfide gas by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The aeration cycle was repeated for 2 days and 90% of the 1,3,5-tri(2-hydroxyethyl) hexahydro-s-triazine solution was regenerated. The solution was then reacted with 2.3 grams of 99.5% hydrogen sulfide gas by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The aeration cycle was repeated for 33 hours and 63% of the 1,3,5-tri(2-hydroxyethyl) hexahydro-s-triazine solution was regenerated.

EXAMPLE 11

Seven and a half grams of a 43% solution of 1,3,5-tri(2-hydroxyethyl)hexahydro-s-triazine, available commercially from Quaker Chemical Corp. that had been previously reacted with 99.5% hydrogen sulfide, commercially from Aldrich Chemical of Milwaukee Wis., to completion, was mixed with 0.17 grams of 1,2-naphthaquinone-4-sulfonic acid sodium salt (97%), available commercially from Aldrich Chemical of Milwaukee Wis. 23 grams of distilled water was added to this mixture. The solution was then stirred and aerated in a 500 ml bottle by bubbling air into the mixture for 6 hours at room temperature (approx. 20° C.) at a flow rate of 33 ml/sec. At the end of the aeration process the 1,3,5-tri(2-hydroxyethyl)hexahydro-s-triazine solution was 75% regenerated.

EXAMPLE 12

An aqueous solution of 1,3,6,8-tricyclotetraaza[4,4,1,1$^{3,8}$]-dodecane was prepared by reacting 50.1 grams of 37 percent formaldehyde available form Borden Chemical of Sheboigan, Wis. in an ice bath with the slow addition of 20.1 grams of 99% ethylenediamine, available from Aldrich Chemical of Milwaukee Wis. with an addition funnel over a period of two hours. The solution was allowed to warm to room temperature (approx. 22° C.) at the end of the two hour addition period. Once synthesized, 34.5 grams of 1,3,6,8-tricyclotetraaza[4,4,1,1$^{3,8}$]-dodecane, was diluted with 120 grams of distilled water and the solution was then reacted with 3.3 grams of 99.5% hydrogen sulfide gas by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. 2.6 grams of 1,2-naphthaquinone-4-sulfonic acid sodium salt (97%), available commercially from Aldrich Chemical of Milwaukee Wis., was added to this mixture. The solution was then stirred and aerated in a 500 ml bottle by bubbling air into the mixture for 2 days at room temperature (approx. 20° C.) at a flow rate of 33 ml/sec. The solution was then reacted with 2.6 grams of 99.5% hydrogen sulfide gas, available commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The aeration cycle was repeated for 1 day before the next scrubbing cycle. The solution was then reacted with 1.8 grams of 99.5% hydrogen sulfide gas by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector.

EXAMPLE 13

Approximately five grams of iodine, available from Aldrich Chemical, Milwaukee, Wis. was added to 50 ml of a 43% solution of 1,3,5-(2-hydroxyethyl)hexahydro-s-triazine that had previously been reacted to completion with 99.5% hydrogen sulfide, available from Aldrich Chemical, Milwaukee, Wis. The mixture was stirred and aerated at room temperature (approx. 20° C.) by bubbling air into the mixture for eight hours at a flow rate of 33 ml/sec. At the end of the eight hour period, the liquid was analyzed on a Varian 200 MHz NMR and found to contain 1,3,5-(2-hydroxyethyl) hexahydro-s-triazine and no detectable level of the spent triazine.

EXAMPLE 14

A 43% solution of 1,3,5-tri(2-hydroxyethyl)hexahydro-s-triazine, available commercially from Quaker Chemical Corp. was placed in a 500 ml glass bottle and reacted to completion with 99.5% hydrogen sulfide, commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The spent solution was then diluted to 25% by weight with tap water. A solution of 25.6 grams of the diluted spent triazine and 0.26 grams of $V_2O_5$, available commercially from Aldrich Chemical of Milwaukee Wis., was placed in a separate 500 ml bottle. The solution was then stirred and aerated in the 500 ml bottle by bubbling air into the mixture for 15 hours at room temperature (approx. 20° C.) at a flow rate of 33 ml/sec. At the end of the aeration process the 1,3,5-tri(2-hydroxyethyl) hexahydro-s-triazine was 79% regenerated.

EXAMPLE 15

A 43% solution of 1,3,5-tri(2-hydroxyethyl)hexahydro-s-triazine, available commercially from Quaker Chemical Corp. was placed in a 500 ml glass bottle and reacted to completion with 99.5% hydrogen sulfide, commercially from Aldrich Chemical of Milwaukee Wis., by bubbling the hydrogen sulfide into the solution at room temperature (approx. 20° C.) at a flow rate of 4.8 ml/min. The bubbling was continued until the presence of hydrogen sulfide was detected in the gas exiting the bottle with a portable hydrogen sulfide gas detector. The spent solution was then diluted to 25% by weight with tap water. A solution of 25.0 grams of the diluted spent triazine and 0.20 grams of copper (II) sulfate, available commercially from Aldrich Chemical of Milwaukee Wis., was placed in a separate 500 ml bottle. The solution was then stirred and aerated in the 500 ml bottle by bubbling air into the mixture for 15 hours at room temperature (approx. 20° C.) at a flow rate of 33 ml/sec. At the end of the aeration process the 1,3,5-tri(2-hydroxyethyl) hexahydro-s-triazine was 97% regenerated.

The present invention may be embodied in other specific forms without departing from the spirit or essential attributes thereof and, accordingly, reference should be made to the appended claims rather than to the foregoing specification as indicated scope of the invention.

We claim:

1. A method for regenerating an at least partially spent aminal comprising, reacting said at least partially spent aminal with: a gas containing an oxidation source selected from the group consisting of air, oxygen, ozone, and mixtures thereof, in the presence of an oxidation catalyst.

2. A method as in claim 1 wherein, said aminal is a reaction product of
  a) an aldehyde and b) a nitrogen containing compound selected from the group consisting of ammonia, primary amines and secondary amines.

3. A method as in claim 2 wherein,
said aldehyde is selected from the group consisting of hydrous and anhydrous forms of formula II

where R is selected from the group consisting of (i) hydrogen; (ii) a substituted or unsubstituted, saturated or unsaturated, linear, branched or cyclic hydrocarbon chain of 1 to 50 carbons; (iii) a substituted or unsubstituted, saturated or unsaturated, linear, branched or cyclic hydrocarbon chain of 1 to 50 carbons comprising at least one hetero atom selected from the group consisting of nitrogen, oxygen, sulfur and halogen; (iv) a substituted or unsubstituted polymeric chain; (v) a substituted or unsubstituted dimer; and (vi) a mono or polyaldehyde; and wherein said nitrogen containing compound has the formula III

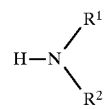

wherein $R^1$ and $R^2$ are independently selected from the group consisting of (i) hydrogen; (ii) a substituted or unsubstituted, saturated or unsaturated, linear, branched or cyclic hydrocarbon chain of 1 to 50 carbons; (iii) a substituted or unsubstituted, saturated or unsaturated, linear, branched or cyclic hydrocarbon chain of 1 to 50 carbons comprising at least one hetero atom selected from the group consisting of nitrogen, oxygen, sulfur and halogen; and (iv) a substituted or unsubstituted polymeric chain; wherein $R^1$ and $R^2$ may be bonded to one another.

4. A method as in claim 3 wherein,
said aldehyde is selected from the group consisting of formaldehyde, paraformaldehyde, glyoxal, acetaldehyde, butyraldehyde, benzaldehyde, N-(2-hydroxyethyl)dioxazine and oleyl aldehyde.

5. A method as in claim 4 wherein, said aldehyde is formaldehyde.

6. A method as in claim 3 wherein, said nitrogen containing compound is selected from the group consisting of ammonia, methylamine, ethylamine, propylamine, isopropyl amine, oleylamine, ethylene diamine, diethylene triamine, dimethylamine, diethylamine, monoethanolamine, diethanolamine, morpholine, piperazine, 3-ethoxypropylamine, 1-methoxyisopropylamine, 2-methoxyethylamine, thiomonoethanolamine and chlorooleylamine.

7. A method as in claim 6 wherein, said nitrogen containing compound is selected from the group consisting of ethylene diamine and monoethanolamine.

8. A method as in claim 1 wherein, said oxidation catalyst has a standard reduction potential of at least −0.4 volts.

9. A method as in claim 8 wherein, said oxidation catalyst has a standard reduction potential from 0.0 volts to 0.9 volts.

10. A method as in claim 9 wherein, said oxidation catalyst has a standard reduction potential from 0.3 volts to 0.8 volts.

11. A method as in claim 1 wherein, said aminal comprises at least one of the compounds selected from the group consisting of compounds of formula I, formula IV and formula V

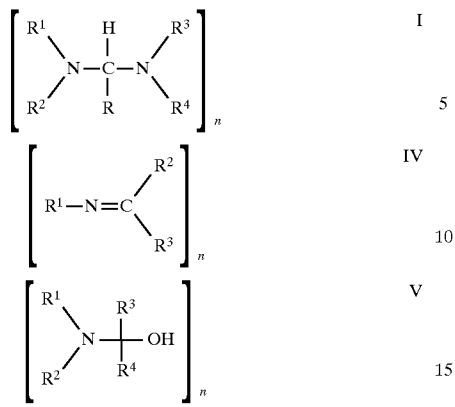

where n is an integer from 1 to 1000 and each of $R^1$, $R^2$, $R^3$, $R^4$, and R is independently selected from the group consisting of (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; and (iv) a substituted or unsubstituted polymeric chain; and wherein $R^1$, $R^2$, $R^3$, $R^4$, and R may be individually bonded to one another.

12. A method as in claim 1 wherein, said oxidation catalyst is selected from the group consisting of halides, quinones, organic peroxides, organic peroxyacids, inorganic peroxides, organic oxides, hydrazines, amino acids, amides, carbamates, carbazides, perchlorates, polyvalent metals and compounds thereof, inorganic oxidizers, and organic dyes.

13. A method as in claim 12 wherein, said oxidation catalyst is selected from the group consisting of quinones, organic peroxyacids, hydrazines and organic dyes.

14. A method as in claim 12 wherein said oxidation catalyst is selected from the group consisting of 1,2, Naphthaquinone-4-sulfonic acid sodium salt, 4-amino-3-hydrazino-5-mercapto-1,2,4-triazole, 2-hydroxy-1,4-naphthaquinone, and metachloroperbenzoic acid.

15. A method as in claim 1 wherein, said at least partially spent aminal is formed through the reaction of an aminal with a sulfide containing gas in a first vessel.

16. A method as in claim 15 wherein, said oxidation source is contacted with said at least partially spent aminal compound in a second vessel separate from said first vessel in which said at least partially spent aminal is reacted with said sulfide containing gas.

17. A method as in claim 15 wherein, said oxidation source is contacted with said at least partially spent aminal compound in said first vessel.

18. A method as in claim 1, further comprising reacting said at least partially spent animal with said oxidation source and up to 99.5% by weight water, in the presence of said oxidation catalyst.

19. A composition for removing hydrogen sulfide from gases comprising an aminal and an oxidation catalyst, wherein said aminal is capable of being regenerated.

20. A composition as in claim 19 wherein, said aminal is a reaction product formed from the reaction between
   a) an aldehyde and
   b) a nitrogen containing compound selected from the group consisting of ammonia, primary amines and secondary amines.

21. A composition as in claim 20 wherein,
   said aldehyde is selected from the group consisting of hydrous and anhydrous forms of formula II where R is selected from the group consisting of (i) hydrogen; (ii) a substituted or unsubstituted, saturated or unsaturated, linear, branched or cyclic hydrocarbon chain of 1 to 50 carbons; (iii) a substituted or unsubstituted, saturated or unsaturated, linear, branched or cyclic hydrocarbon chain of 1 to 50 carbons comprising at least one hetero atom selected from the group consisting of nitrogen, oxygen, sulfur and halogen; (iv) a substituted or unsubstituted polymeric chain; (v) a substituted or unsubstituted dimer; and (vi) a mono or polyaldehyde; and wherein said nitrogen containing compound has the formula III

wherein $R^1$ and $R^2$ are independently selected from the group consisting of (i) hydrogen; (ii) a substituted or unsubstituted, saturated or unsaturated, linear, branched or cyclic hydrocarbon chain of 1 to 50 carbons; (iii) a substituted or unsubstituted, saturated or unsaturated, linear, branched or cyclic hydrocarbon chain of 1 to 50 carbons comprising at least one hetero atom selected from the group consisting of nitrogen, oxygen, sulfur and halogen; (iv) a substituted or unsubstituted polymeric chain; and wherein $R^1$ and $R^2$ may be bonded to one another.

22. A composition as in claim 21 wherein, said aldehyde is selected from the group consisting of formaldehyde, paraformaldehyde, glyoxal, acetaldehyde, butyraldehyde, benzaldehyde, N-(2-hydroxyethyl)dioxazine and oleyl aldehyde.

23. A composition as in claim 22 wherein, said aldehyde is formaldehyde.

24. A composition as in claim 21 wherein, said nitrogen containing compound is selected from the group consisting of ammonia, methylamine, ethylamine, propylamine, isopropyl amine, oleylamine, ethylene diamine, diethylene triamine, dimethylamine, diethylamine, monoethanolamine, diethanolamine, morpholine, piperazine, 3-ethoxypropylamine, 1-methoxyisopropylamine, 2-methoxyethylamine, thiomonoethanolamine and chlorooleylamine.

25. A composition as in claim 24 wherein, said amine is selected from the group consisting of ethylene diamine and monoethanolamine.

26. A composition as in claim 19 wherein, said oxidation catalyst has a standard reduction potential of at least −0.4 volts.

27. A composition as in claim 26 wherein, said oxidation catalyst has a standard reduction potential from 0.0 volts to 0.9 volts.

28. A composition as in claim 27 wherein, said oxidation catalyst has a standard reduction potential from 0.3 volts to 0.8 volts.

29. A composition as in claim 24 wherein, said reaction product comprises at least one of the compounds selected from the group consisting of compounds of formula I, formula IV and formula V:

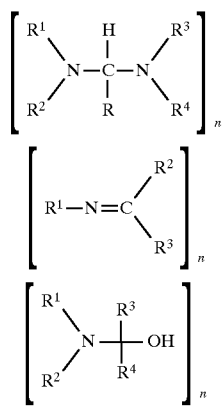

where n is an integer from 1 to 1000 and each of $R^1$, $R^2$, $R^3$, $R^4$, and R is independently selected from the group consisting of (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; and (iv) a substituted or unsubstituted polymeric chain; wherein $R^1$, $R^2$, $R^3$, $R^4$, and R may be individually bonded to one another.

30. A composition as in claim 22 wherein, said oxidation catalyst is selected from the group consisting of halides, quinones, organic peroxides, organic peroxyacids, inorganic peroxides, organic oxides, hydrazines, amino acids, amides, carbamates, carbazides, perchlorates, polyvalent metals and compounds thereof, inorganic oxidizers, and organic dyes.

31. A composition as in claim 19 wherein, said oxidation catalyst is selected from the group consisting of quinones, organic peroxyacids, hydrazines and organic dyes.

32. A composition as in claim 30 wherein, said oxidation catalyst is selected from the group consisting of 1,2, Napthaquinone-4-sulfonic acid sodium salt, 4-amino-3-hydrazino-5-mercapto-1,2,4-triazole, 2-hydroxy-1,4-naphthaquinone, and metachloroperbenzoic acid.

33. A composition as in claim 19, further comprising up to 99.5% by weight water.

* * * * *